United States Patent [19]

Silverstein et al.

[11] Patent Number: 4,582,067

[45] Date of Patent: Apr. 15, 1986

[54] METHOD FOR ENDOSCOPIC BLOOD FLOW DETECTION BY THE USE OF ULTRASONIC ENERGY

[75] Inventors: Fred E. Silverstein, Seattle; Roy W. Martin, Redmond; David A. Gilbert, Seattle, all of Wash.

[73] Assignee: Washington Research Foundation, Seattle, Wash.

[21] Appl. No.: 466,123

[22] Filed: Feb. 14, 1983

[51] Int. Cl.[4] .......................................... A61B 10/00
[52] U.S. Cl. .................................................... 128/663
[58] Field of Search ........................ 128/4, 660–661, 128/663

[56] References Cited

U.S. PATENT DOCUMENTS

| | | | |
|---|---|---|---|
| 3,827,115 | 8/1974 | Bom | 29/25.35 |
| 3,938,502 | 2/1976 | Bom | 128/2 V |
| 4,319,580 | 3/1982 | Colley et al. | 128/661 |
| 4,354,500 | 10/1982 | Colley et al. | 128/663 |
| 4,354,501 | 10/1982 | Colley et al. | 128/663 |
| 4,354,502 | 10/1982 | Colley et al. | 128/663 |

OTHER PUBLICATIONS

Loh, C. L. et al, "The Differentiation of Bile Ducts and Blood Vessels Using a Pulsed Doppler System", UTS in Med. & Biol., vol. 4, No. 1, pp. 37–49 (1978).
Hisanaga, K. et al, "A New Trans—Digestive Tract Scanner with a Gastro-Fiber-Scope", Proc. 23AIUM 1978.
Hisanaga, K. et al, "A New Real—Time Sector Scanning System . . ." UTS in Medicine, vol. 4, White et al. editors, Plenum Press.
Histand, M. B. et al, "UTS Pulsed Doppler Transesophageal Measurement of Aortic Haemodynamics", Ultrasonics Sep. 1979.
Reid et al., "A New Doppler Flowmeter System and its Operation with Catheter Mounted Transducers," appearing in *Cardiovascular Applications of Ultrasound*, Reneman, ed., pp. 183-192, 1974.
Martin et al., "Ultrasonic Catheter Tip Instrument for Measurement of Vessel Cross-Sectional Area", Proceedings, 27th Annual Conference on Engineering in Medicine and Biology, v. 16, p. 186, 1974.
Martin et al., "An Ultrasonic Catheter Tip Instrument for Measuring Volume Blood Flow", Proceedings, 1975 Ultrasonics Symposium, pp. 13-17, 1975.
Martin et al., "An Ultrasonic Catheter Tip Instrument for Measuring Volume Blood Flow", IEEE Transactions on Sonics and Ultrasonics, v. SU-23, No. 3, p. 207 1976.

(List continued on next page.)

Primary Examiner—Kyle L. Howell
Assistant Examiner—Francis J. Jaworski
Attorney, Agent, or Firm—Christensen, O'Connor, Johnson & Kindness

[57] ABSTRACT

Various forms of a catheter that is sized to pass through the biopsy channel of an endoscope include an elongated catheter tube of flexible material and an ultrasonic probe carried by the catheter tube adjacent its tip. The forms include: a papillotome catheter (FIGS. 1 and 3); catheters for general endoscopic and nonendoscopic applications (FIGS. 4, 7A through 7C, 8A through 8B, 10A through 10B, and 11); and, a sclerosing catheter (FIGS. 13 through 15). These catheters may be used to determine the location of the retroduodenal artery in endoscopic papillotomy (FIGS. 2, 5, and 6), to evaluate and treat esophageal varices (FIGS. 9 and 12), or generally to detect blood flow in a biological structure within the body. Depending on the application, the ultrasonic field provided by the ultrasonic probe may be either transverse or parallel to the longitudinal axis of the catheter tube and may be either highly directional, omnidirectional, or sectorial. The ultrasonic probe is coupled to a pulsed Doppler circuit (FIG. 16) by an isolation circuit (FIGS. 17 through 20) that provides electrical isolation and RFI suppression. The Doppler circuit is designed to enhance close proximity detection of blood flow, to limit the range of the probe's ultrasonic field, and to distinguish between arterial blood flow, venous blood flow, and vessel wall motion.

4 Claims, 24 Drawing Figures

OTHER PUBLICATIONS

Martin et al., "Stroke Volume Measurement with an Ultrasonic Catheter Tip System", appearing in *Ultrasound in Medicine*, White et al., ed., v. 3A, pp. 23-39, 1978.

Martin et al., "Signal Enhancement for Automatic Identification of Arterial Wall Echoes from an Intravessel Scanner", appearing in *Ultrasound in Medicine*, White et al., ed., v. 4, pp. 417-431, 1978.

Colley et al., "Intravascular Doppler Catheter for Detection of Air Emboli", *Proc. of Amer. Soc. Anesthesiologists Symposium*, 1978.

Martin et al., "Intravascular and Esophageal Ultrasonic Catheters for Detection of Air Emboli", *Proc. of American Institute of Ultrasound Technical Specialists*, 1978 *Annual Meeting*, 1978.

Martin et al., "Intravascular and Esophageal Ultrasonic Catheters for Detection of Air Emboli", *Reflections*, 1978.

Poore, "1 mm Catheter Tip Doppler Probe Using a Single Crystal and Bridge", *Ultrasonic Imaging*, v. 1, pp. 101-103, 1979.

Beckly et al., "The Use of a Doppler Ultrasound Probe for Localising Arterial Blood Flow During Upper Gastrointestinal Endoscopy", *Endoscopy*, v. 14, pp. 146-147, Jul. 1982.

McCormick et al., "Doppler Ultrasound Probe for Assessment of Blood—Flow in Oesophageal Varices", *The Lancet*, pp. 677-678, Mar. 1983.

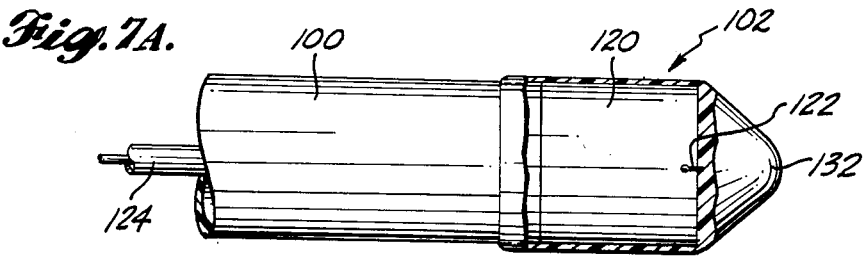
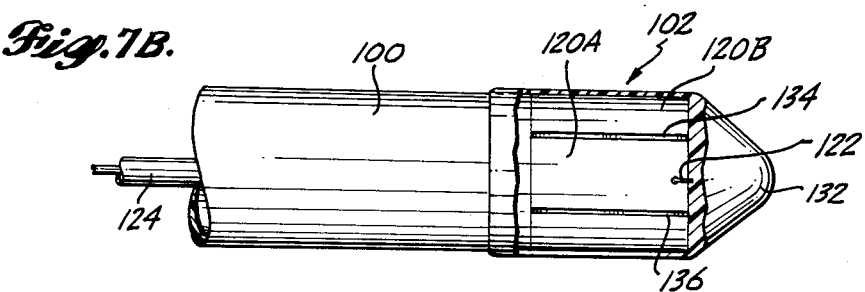
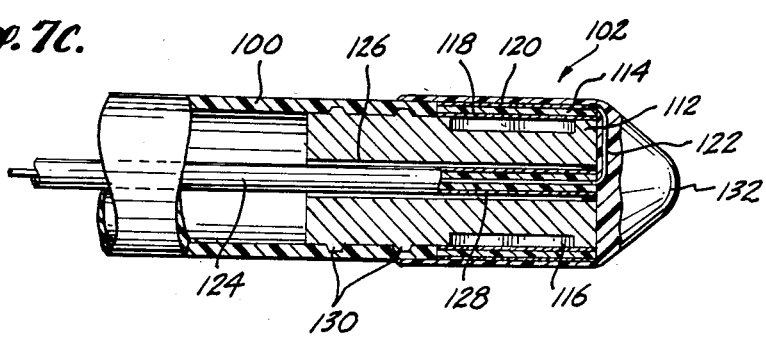
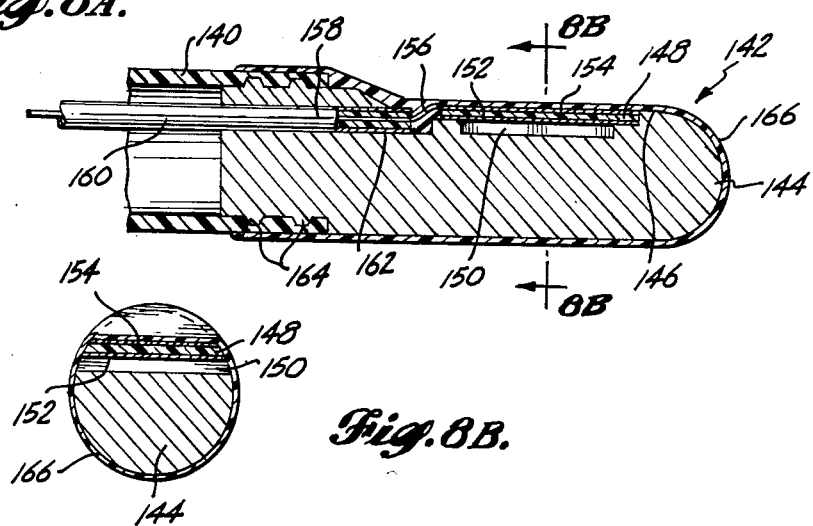

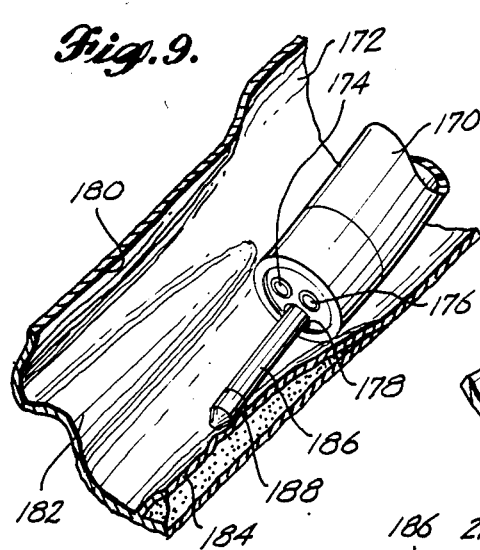
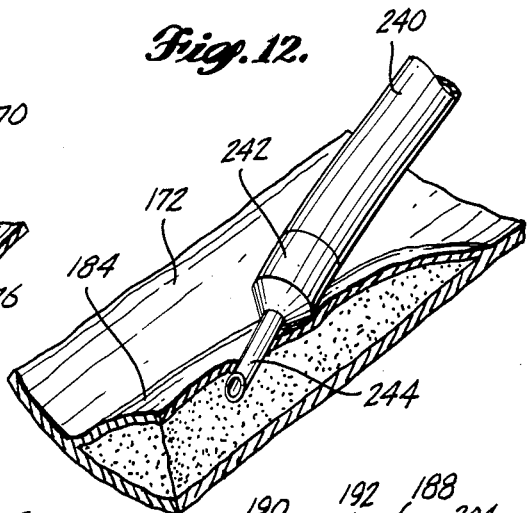
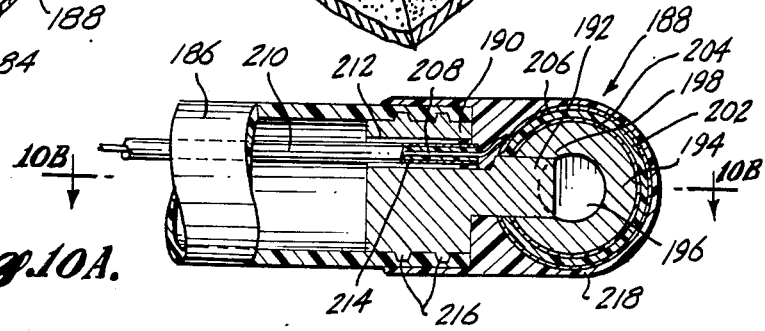
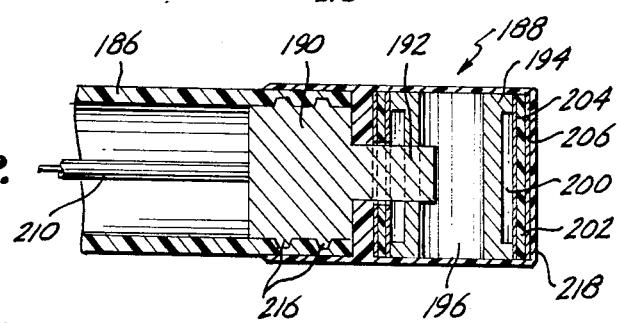
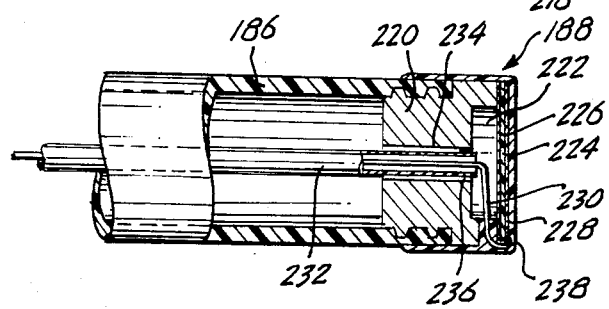

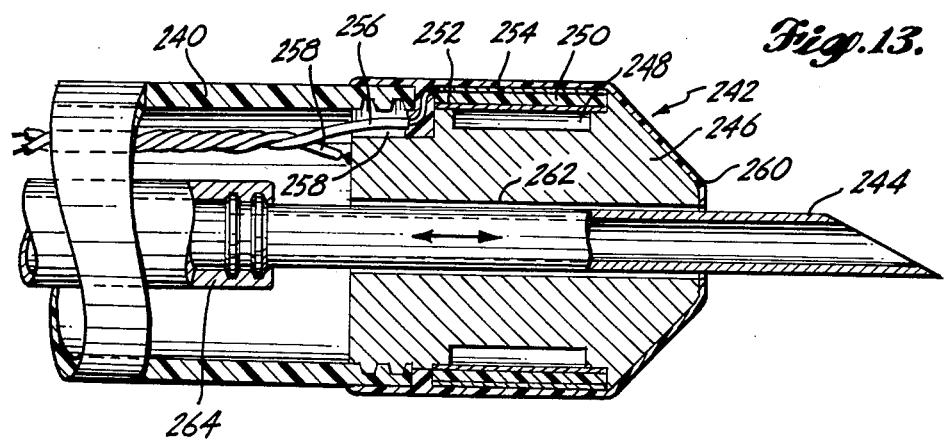
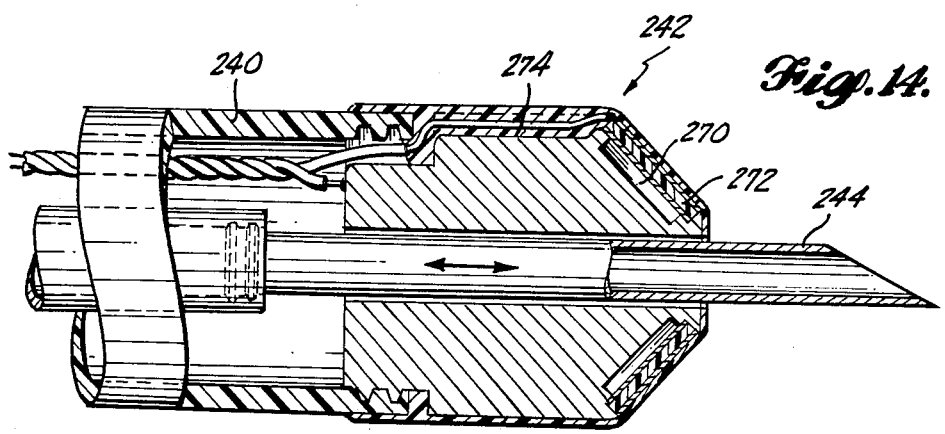
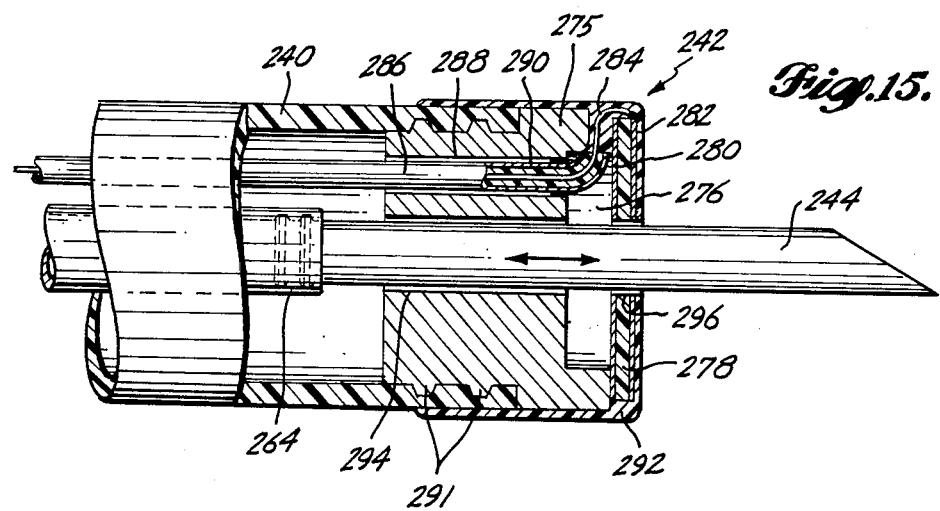

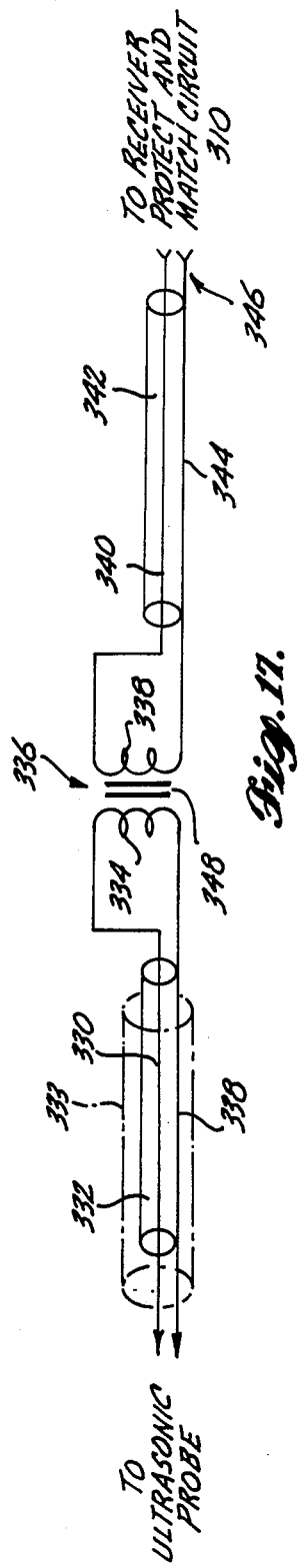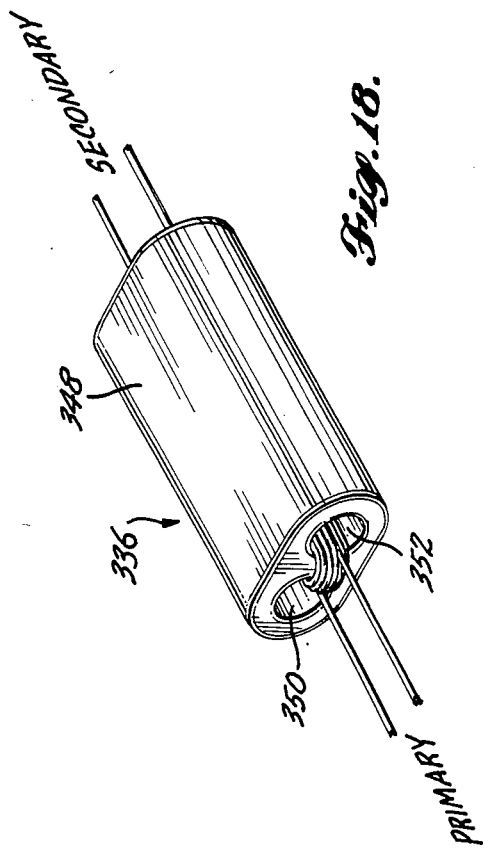

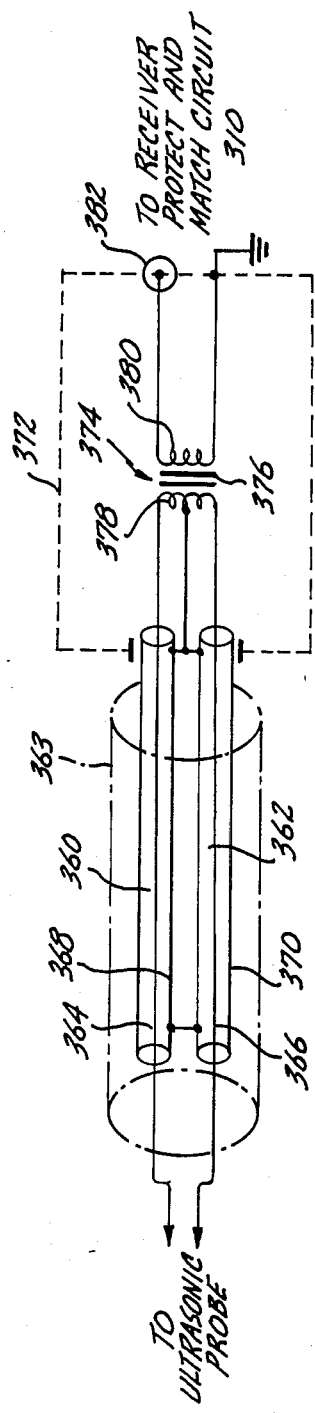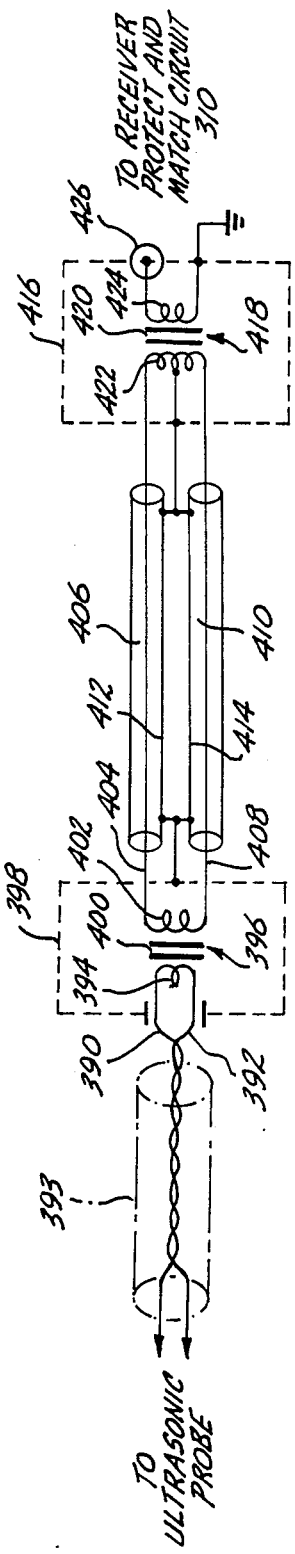

METHOD FOR ENDOSCOPIC BLOOD FLOW DETECTION BY THE USE OF ULTRASONIC ENERGY

FIELD OF THE INVENTION

This invention generally relates to diagnostic and therapeutic methods and apparatus using ultrasonic energy, and more particularly to such methods and apparatus particularly adapted for use with an endoscope to provide blood flow detection.

BACKGROUND OF THE INVENTION

Flexible endoscopes including optical fibers are used for a variety of endoscopic procedures such as endoscopic papillotomy and the evaluation of esophageal varices, arteriovenous malformations, ulcer vessels, ischemic bowel disease, and polyps.

Endoscopic papillotomy is a nonoperative technique which enables relief of common bile duct obstruction due to retained gallstones. In this technique, a flexible endoscope is inserted into the duodenum and advanced until the entrance to the common bile duct and the pancreatic duct (i.e., the papilla of Vater) can be visualized. A papillotome catheter is then passed through the biopsy channel of the endoscope until the catheter tip exits from the endoscope tip, and the endoscope tip is remotely manipulated and the papillotome catheter is concurrently advanced so as to insert the papillotome catheter into the common bile duct. Along its side adjacent its tip, the papillotome catheter carries an elongated wire that can be remotely bowed so as to bear upon the roof of the papilla. By passing an electrosurgical current through the wire when the papillotome catheter has been appropriately positioned and bowed, the roof of the papilla of Vater may be cut so as to enlarge the papilla orifice. After withdrawal of the papillotome catheter, the retained gallstones in the common bile duct may naturally migrate into the duodenum or may be removed by a grasping device passed through the biopsy channel of the endoscope.

In certain patients, the retroduodenal artery is quite close to the papilla and may be cut by the papillotome catheter, thereby leading to morbidity and mortality complications. To reduce the risk of endoscopic papillotomy, it is highly desirable to determine the location of the retroduodenal artery relative to the papilla of Vater by detecting the presence and characteristics of blood flow in the retroduodenal artery.

Esophageal varices are dilated veins on the inner surface of the esophagus, most typically resulting from cirrhosis of the liver, and quite often bleed. Although pharmaceutical and surgical methods typically are used to treat esophageal varices, an endoscopic technique also may be used in which a flexible endoscope is inserted into the esophagus and advanced until a varix is visualized. A catheter having a hollow needle at its tip is then passed through the biopsy channel of the endoscope so that the needle exits from the endoscope tip, and the endoscope tip is remotely manipulated and the catheter is concurrently advanced until the needle is inserted into the varix. A sclerosing agent is then injected through the catheter and the needle into the varix in order to thrombose or clot the varix.

Occasionally, a heavy esophageal mucosal fold may mimic the appearance of a varix. It is therefore highly desirable to determine if the visualized target is a varix by the detection of venous flow before needle insertion and sclerosing agent injection. It is also highly desirable to determine the effect of the injected sclerosing agent in the event the target is a varix by the detection of a reduction in and eventual absence of venous flow.

Another type of lesion which causes problematic gastrointestinal bleeding is that of an arteriovenous malformation which can be visualized through the use of a flexible endoscope as a small red dot on the mucosa of the gut. Unfortunately, it is often very difficult to tell if such a red spot is an adherent clot, a petechiae or an arteriovenous malformation. It is therefore highly desirable to positively determine such a red spot as an asteriovenous malformation by the detection of arterial blood flow.

In a similar manner, the evaluation of ulcerations in the stomach or duodenum and of techniques being used to thrombose such ulcerations, the diagnosis of ischemic bowel disease, and the evaluation of the size of the blood vessels in the stalks of gastrointestinal polyps by use of a flexible endoscope would be facilitated by detecting the presence and characteristics of proximate blood flow.

Rigid endoscopes are used for a variety of endoscopic procedures such as peritoneoscopy, arthroscopy, proctoscopy, thoracoscopy and cystoscopy. As with flexible endoscopic procedures, rigid endoscopic procedures would benefit immensely from the detection of the presence and characteristics of proximate blood flow. For example, in the examination of an organ such as the liver in peritoneoscopy, a mass may be encountered. If the mass is an arteriovenous malformation, biopsy of the mass may result in severe life-threatening hemorrhage which could be prevented by the prior determination of the mass as an arteriovenous malformation through the detection of arterial blood flow therein.

In addition to the endoscopic procedures discussed, many surgical procedures would benefit from the detection of proximate blood flow. As examples, the detection of arterial blood flow proximate the site of an abdominal aneurysm repair or a coronary artery bypass would allow assessment of the success of the surgical procedure. Just as it is often difficult for the endoscopist to determine if a biological structure is vascular, the same problem may occur for the surgeon, and it may be very important to determine if a biological structure about to be biopsied or removed is highly vascular.

Besides detecting blood flow during endoscopic and surgical procedures, the long-term monitoring of blood flow and differentiation of arterial from venous flow in biological structures is highly desirable. For example, long-term monitoring of blood flow in an artery would permit simultaneous monitoring of heart rate and of an indication of impending shock or a change in cardiac output.

In the prior art, detection of blood flow in biological structures is accomplished by evaluation of a Doppler signal obtained from an ultrasonic transducer that ensonifies the biological structure. As of the present, no practical methods or apparatus providing a Doppler signal have been devised which can be successfully used with the endoscopic, surgical and monitoring diagnostic and therapeutic methods discussed above. In order to meet the requirements of such methods, the ultrasonic apparatus must be small in diameter and flexible so as to be capable of being passed through the biopsy channel of an endoscope or otherwise inserted into the body, must be nontoxic and must be resistant to bodily fluids when left within the body, must be capable of detecting blood flow in the biological structure of interest and of distinguishing the detected blood flow from that in adjacent biological structures, and must be capable of detecting the characteristics of blood flow so as to distinguish between arterial and venous flow.

SUMMARY OF THE INVENTION

In its broadest sense, the invention resides in a method for identifying and monitoring an intracorporeal biological structure. The method comprises the steps of: inserting an endoscope into the body; visualizing, through the endoscope, the location of the biological structure; passing a catheter including an ultrasonic probe through a biopsy channel of the endoscope and into proximity to the biological structure; and, monitoring a Doppler signal obtained from the ultrasonic probe for that Doppler signal characteristic of blood flow in the biological structure.

Exemplary applications in which such a method may be used are endoscopic papillotomy and the evaluation and treatment of esophageal varices.

In endoscopic papillotomy, the location of the retroduodenal artery relative to the papilla of Vater may be determined by inserting a flexible, side-viewing endoscope into the duodenum. After visualizing the papilla through the endoscope, a catheter including an ultrasonic probe having a transverse, sectorial, range-limited field is passed through a biopsy channel of the endoscope, through the papilla, and into the common bile duct so that the ultrasonic field is directed toward the retroduodenal artery. The catheter is advanced and a Doppler signal obtained from the probe is monitored until the Doppler signal is characteristic of arterial blood flow. Then, the amount by which the catheter has been advanced past the papilla is visualized through the endoscope.

Alternatively, the probe of the catheter may have an omni-directional field. Such a catheter may be brought into contact with the duodenum and advanced along the duodenum until the Dopper signal obtained from the probe is characteristic of arterial blood flow. The location of the probe relative to the papilla is then visualized through the endoscope.

In the evaluation of esophageal varices, a flexible, end-viewing endoscope is inserted into the esophagus. After visualizing a protrusion in the esophagus through the endoscope, a catheter including an ultrasonic probe having a range-limited ultrasonic field is passed through a biopsy channel of the endoscope and into the esophagus until the probe contacts the protrusion. A Doppler signal obtained from the ultrasonic probe is then monitored for that Doppler signal characteristic of venous blood flow.

BRIEF DESCRIPTION OF THE DRAWINGS

The invention can best be understood by reference to the following portion of the specification, taken in conjunction with the accompanying drawings in which:

FIGS. 7A, 7B and 7C are longitudinal cross-sectional views of a catheter including one form of a side-viewing ultrasonic probe;

FIGS. 8A and 8B are respective longitudinal and transverse cross-sectional views of a catheter including another form of a side-viewing ultrasonic probe;

FIG. 9 is a pictorial view illustrating the use of a catheter including an ultrasonic probe in the evaluation of esophageal varices;

FIGS. 10A and 10B are longitudinal cross-sectional views of a catheter including one form of an end-viewing ultrasonic probe;

FIG. 11 is a longitudinal cross-sectional view of a catheter including another form of an end-viewing ultrasonic probe;

FIG. 12 is a pictorial view illustrating the sclerosing of an esophageal varix by the use of a sclerosing catheter including an ultrasonic probe and a sclerosing needle;

FIG. 13 is a longitudinal cross-sectional view of a sclerosing catheter including a side-viewing ultrasonic probe;

FIG. 14 is a longitudinal cross-sectional view of a sclerosing catheter including one form of an end-viewing ultrasonic probe;

FIG. 15 is a longitudinal cross-sectional view of a sclerosing catheter including another form of an end-viewing ultrasonic probe;

FIG. 17 is an electrical schematic of an isolation circuit for coupling the ultrasonic probe of such a catheter to the Doppler circuit;

FIG. 18 is a pictorial view of a transformer included in the isolation circuit; and, FIGS. 19 and 20 are electrical schematics of additional isolation circuits.

DESCRIPTION OF THE PREFERRED EMBODIMENT

The invention initially will be described with reference to its use with endoscopic papillotomy and then with respect to its use in the evaluation and treatment of esophageal varices. The invention is not limited to these two techniques, however, and is broadly applicable to intracorporeal blood flow detection in conjunction with many diagnostic and therapeutic methods such as those previously discussed.

Figure 1:
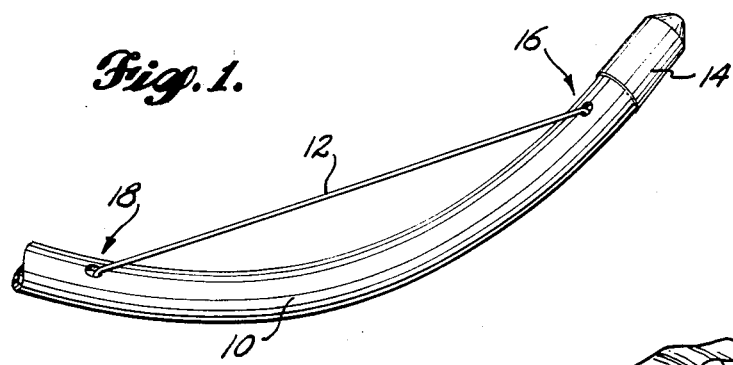
FIG. 1 is a pictorial view of a papillotome catheter including an ultrasonic probe.

Referring now to FIG. 1, a papillotome catheter similar to those previously known and used but modified for the detection of blood flow includes as its major components an elongated, cylindrical tube 10 of flexible material, an elongated wire 12 carried by tube 10, and an ultrasonic probe 14 disposed at the tip of tube 10. As will be discussed in conjunction with FIG. 3, one end of wire 12 terminates within tube 10 proximate ultrasonic probe 14. From that end, wire 12 extends through an opening 16 in tube 10, along the exterior of tube 10, then back through an opening 18 in tube 10 and thence within and through the remaining length of tube 10 to and beyond its distal end (not illustrated). Normally, the portion of the catheter illustrated in FIG. 1 is yieldably biased to a substantially linear configuration wherein wire 12 lies on the exterior of tube 10. When tension is applied to the distal end of wire 12, however, the catheter is bowed to the configuration illustrated in FIG. 1 so that wire 12 bears against body tissue which may then be cut by the passage of an electrosurgical current through wire 12.

Ultrasonic probe 14 includes an ultrasonic transducer that is capable of ultrasonic energy transmission and reception in directions transverse (i.e., at an angle) and preferably normal to the longitudinal axis of tube 10. The ultrasonic transducer is connected to a Doppler circuit described hereinafter with reference to FIG. 16 by means of leads (not illustrated) disposed within tube 10. As described in detail hereinafter, the ultrasonic transducer within ultrasonic probe 14 is provided with a high frequency electrical signal (the transmitted signal) which is converted by the ultrasonic transducer into ultrasonic energy. Returned ultrasonic energy is converted by the ultrasonic transducer into a corresponding electrical signal (the received signal) which is compared in the Doppler circuit with the transmitted signal to develop a Doppler signal related to the frequency shift between the transmitted signal and the received signal occasioned by the movement of objects including blood through the region ensonified by the ultrasonic transducer.

Figure 2:
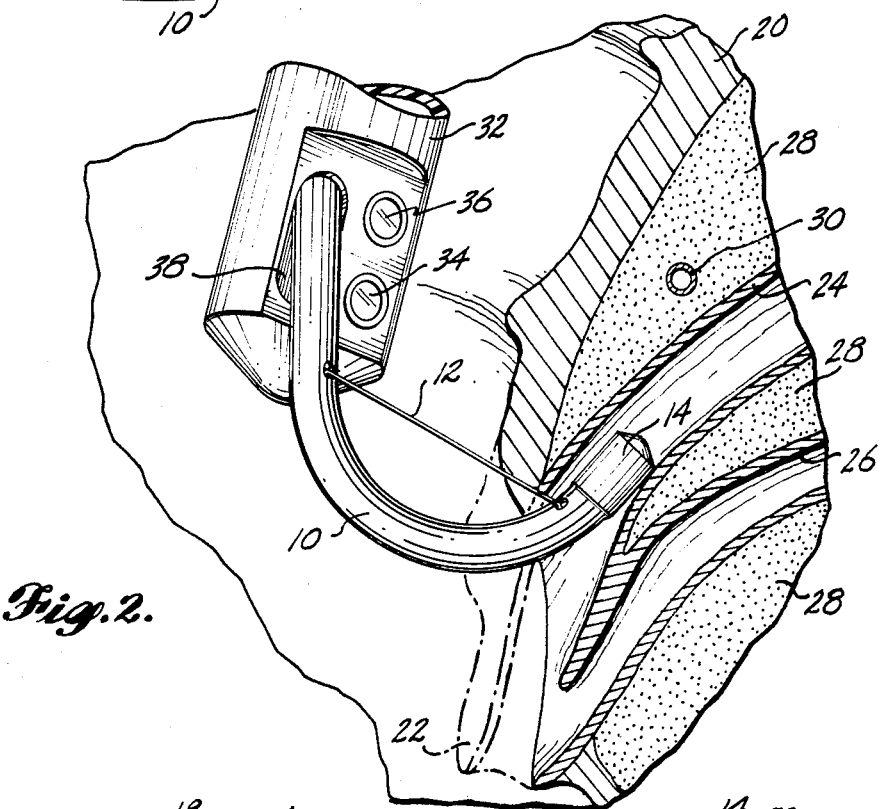
FIG. 2 is a pictorial view illustrating the use of the papillotome catheter of FIG. 1 in endoscopic papillotomy.

Referring now to FIG. 2, a simplified pictorial view of the anatomy in the region of interest in endoscopic papillotomy includes the descending duodenum 20 into which protrudes the papilla of Vater 22. The papilla includes an orifice communicating with both the common bile duct 24 and the pancreatic duct 26. Typically, common bile duct 24 and pancreatic duct 26 are surrounded by pancreatic tissue 28 which extends to the duodenum 20. A major blood supply to common bile duct 24 is provided by the retroduodenal artery 30, a portion of which passes between common bile duct 24 and duodenum 20.

The technique of endoscopic papillotomy is used in the treatment of gallstones that are retained in common bile duct 24. In this technique, a flexible, side-viewing endoscope 32 having optical fibers 34 and 36 and a biopsy channel 38 terminating in its side adjacent its tip is inserted into duodenum 20 and advanced until papilla 22 can be visualized through an optical system of the endoscope including optical fibers 34 and 36. The papillotome catheter of FIG. 1 is then inserted into and advanced along biopsy channel 38 until the catheter tip exits from the biopsy channel. By remote manipulation of the endoscope and catheter tips and by concurrent advancement of the catheter, the catheter tip is passed through the orifice of papilla 22 and into common bile duct 24 so that wire 12 faces the roof or upper portion of the papilla. Remote tension is then applied to wire 12 so that the papillotome catheter assumes its bowed configuration to press wire 12 against the upper portion of the papilla, and a radio frequency electrosurgical current is then passed through a circuit including wire 12 and a ground plate (not illustrated) attached to the patient so as to cut the upper portion of the papilla as illustrated. Upon withdrawal of the papillotome catheter, the retained gallstones may be removed by a grasping device passed through biopsy channel 38 and the now-enlarged orifice of the papilla into common bile duct 24, or, may be allowed to naturally migrate into duodenum 20 through the now-enlarged orifice of the papilla.

Generally, the portion of retroduodenal artery 30 illustrated in FIG. 2 is more than 3 cm from the orifice of papilla 22. In a significant number of patients, however, this distance may be less than 3 cm and may be as small as 1.0 cm. Therefore, there is the distinct possibility that cutting of the papilla in endoscopic papillotomy may also cut the retroduodenal artery, leading to hemorrhage and other complications. It is therefore highly desirable to determine the location of the retroduodenal artery relative to the papilla orifice. In doing so, the papillotome catheter is advanced in its normal, unbowed configuration along common bile duct 24 and the Doppler signal obtained from the ultrasonic transducer in ultrasonic probe 14 is monitored until that Doppler signal characteristic of arterial blood flow is obtained. The amount by which the papillotome catheter has been inserted into common bile duct 24 may then be visualized by use of endoscope 32, allowing an estimate to be made of the location of retroduodenal artery 30 relative to the orifice of papilla 22. If the retroduodenal artery is found to be too close to the papilla orifice, a decision may be made to abort endoscopic papillotomy and to treat the gallstones with pharmaceutical or surgical methods.

In order to provide successful detection of intracorporeal blood flow by means of an apparatus including a catheter having an ultrasonic probe, a number of requirements must be met.

First, the ultrasonic probe must be small enough so that it can be passed through the biopsy channel of an endoscope while yet allowing the biopsy channel to be alternately or simultaneously shared for other purposes. In this regard, the papillotome catheters used in the past for endoscopic papillotomy have an outer diameter of 1.8 mm, so the diameter of the catheter tube and of the ultrasonic probe preferably are equal to or less than that diameter.

Second, the apparatus must be capable of detecting blood flow in the region of interest, a task which is made quite difficult by the limited control available for positioning of the ultrasonic probe in endoscopic applications.

Third, the apparatus must be able to detect blood flow within 1 mm of the probe. In the region of interest in endoscopic papillotomy illustrated in FIG. 2, the maximum thickness of pancreatic tissue 28 between common bile duct 24 and duodenum 20 is approximately 1.5 to 2.0 cm, whereas the minimum thickness of such tissue (i.e., that adjacent papilla 22) is approximately 3 mm. In some cases, the retroduodenal artery 30 may be located about 1 mm from the adjacent surface of common bile duct 24.

Fourth, the apparatus must be safe to use. Since the probe is to be placed in the body in close proximity to the heart and other vital organs, electrical safety is especially important. In the endoscopic papillotomy application, the presence of the probe within the common bile duct requires that the probe be nontoxic and that the probe be resistant to bodily fluids within the duct.

Fifth, it is necessary in many applications, including those of endoscopic papillotomy and in the valuation and treatment of esophageal varices, to limit the range of the apparatus to about 4 to 5 mm in order that blood flow occurring in the body outside of the particular region of interest does not mask blood flow within the region of interest.

Sixth, the apparatus must be capable not only of detecting blood flow, but also of characterizing the detected blood flow as either arterial flow or venous flow and of distinguishing such flow from other components of motion in the region of interest, such as vessel wall motion.

Specific attention to these requirements has been given in the design of not only the catheter but also the Doppler circuit with which the catheter is used.

Figure 3:
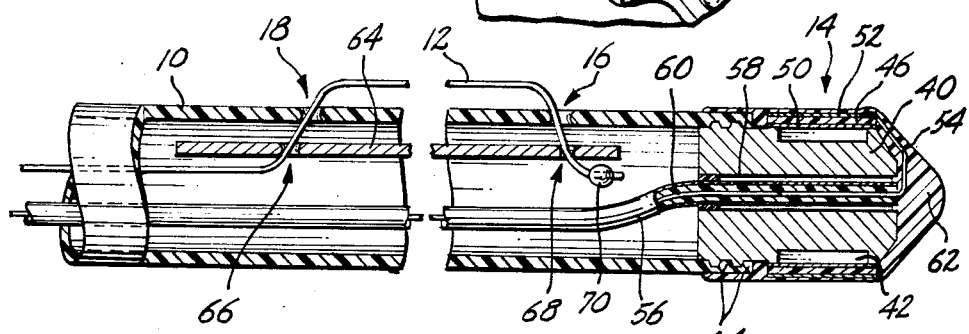
FIG. 3 is a longitudinal cross-sectional view of the papillotome catheter of FIG. 1.

Now referring to FIG. 3, ultrasonic probe 14 includes a substantially cylindrical member 40 of a metallic (e.g., brass) material or of a plastic (e.g., acrylic) material whose exterior surface is covered with a layer of electrically conductive material, such as a conductive epoxy resin or a metallic plating. Around its periphery, member 40 is provided with an annular groove 42 and with spaced-apart, annular ridges 44. The outer diameter of that portion of member 40 bearing ridges 44 is substantially equal to the inner diameter of tube 10 so that member 40 may be inserted into the end of tube 10 and retained therein by the engagement of ridges 44 with the inner wall of the tube. Tube 10 preferably is composed of polyethylene or Teflon TM having an outer diameter of approximately 1.8 mm and a length in the range of 120 cm to 200 cm. An ultrasonic transducer 46 comprising an annular, cylindrical ring of piezoelectric material having metallic, conducting layers 50, 52 formed on its inner and outer cylindrical surfaces, respectively, is disposed on member 40 and overlies groove 42. The outer diameter of transducer 46 is preferably equal to that of tube 10. Inner conductive layer 50 is electrically connected to member 40 by soldering or by the use of an electrically conductive epoxy resin, and outer conductive layer 52 is electrically connected to the center conductor 54 of a microcoaxial cable 56 passing through a central, longitudinal bore 58 within member 40. The electrical connection of inner conductive layer 50 to member 40 also serves to secure transducer 46 to member 40. An outer conductive sheath 60 of cable 56 is terminated within bore 58 and is electrically connected to member 40. In place of cable 56, a twisted pair of wires may also be used. The catheter is completed by a coating 62 of a nonconductive epoxy resin that forms a smoothly rounded tip of the catheter covering and insulating center conductor 54 and that forms a thin layer extending from that tip over transducer 46 and onto an adjacent portion of tube 10.

A thin, flat and elongated spring 64 is disposed within tube 10 adjacent probe 14. Wire 12 passes through an opening 66 in spring 64, through opening 18 in tube 10, along the exterior of tube 10, back through opening 16 in tube 10, and through an opening 68 in spring 64. A ferrule 70 is crimped or welded to the end of wire 12 and prevents wire 12 from being pulled out through openings 68 and 16 when tension is applied to wire 12. Spring 64 tends to maintain the catheter in a linear configuration as illustrated in FIG. 3. When tension is applied to wire 12 so that the catheter assumes its bowed configuration as illustrated in FIG. 1, spring 64 further serves to prevent the flexible material of tube 10 from being cut or otherwise deformed by wire 12 and ferrule 70. In place of spring 64, an elongated coil spring similar to that found in prior papillotome catheters may be used provided that sufficient space remains within tube 10 for wire 12 and cable 56.

Wire 12 and cable 56 extend from the catheter tip illustrated in FIG. 3 along the length of the catheter and exit from the distal end thereof. The exiting end of wire 12 is connected to an appropriate source of an electrosurgical current (not illustrated), and the exiting center conductor 54 and outer conductive sheath 60 of cable 56 are connected through an isolation circuit described hereinafter in conjunction with FIGS. 17–20 to the Doppler circuit described hereinafter in conjunction with FIG. 16.

The catheter illustrated in FIG. 3 is assembled in the following manner. Openings 16 and 18 are formed near the end of tube 10. One end of wire 12 is then inserted through opening 68 in spring 64 and the resultant assembly is inserted into tube 10. The end of wire 12 is then advanced until it exits from opening 16, back through opening 18 and opening 66, and then to the distal end of tube 10 (not illustrated). At this point, ferrule 70 is applied to the other end of wire 12 to complete the assembly of wire 12 and spring 64 within tube 10.

After member 40 has been fabricated by a technique appropriate to the material thereof, ultrasonic transducer 46 is fitted thereon and inner conductive layer 50 thereof is electrically connected to member 40. Cable 56 is passed through the entire length of tube 10, the end of cable 56 is appropriately stripped, and the stripped portion is inserted through bore 58 in member 40. Inner conductor 54 is then electrically connected to outer conductive layer 52 of ultrasonic transducer 46 and outer conductive sheath 60 is electrically connected to member 40 within bore 58. Member 40 is then inserted into the end of tube 10. Either prior to or subsequent to this step, the periphery of tube 10 adjacent member 40 is treated with a solution which permits chemical bonding to the material of tube 10. For example, a solution such as Tetra Etch TM, specially designed for pre-treating Teflon for the purpose of chemical bonding, may be used. The catheter tip is then dipped into liquid, uncured epoxy resin so that a portion of tube 10 is contained within the resin, removed, and heat treated until the resin has cured.

The small size requirement of ultrasonic probe 14 is met by member 40 that provides a solid, stable and accurate base to which ultrasonic transducer 46 may be secured and electrically connected and that permits the probe to be inserted into and retained at the end of a conventional catheter tube such as tube 10. By the use of a pulsed Doppler approach as discussed hereinafter, a single transducer can be used for both the transmission and reception of ultrasonic energy, thereby making it easier to meet the small size requirement in fabrication of the probe.

Because it may be difficult to control the position of the probe in endoscopic applications, a highly directional transducer is generally undesirable in such applications. This problem is addressed by the use of the annular, cylindrical form of ultrasonic transducer 46 that provides an unfocused ultrasonic field transverse and substantially normal to the longitudinal axis of tube 10. Although the ultrasonic field may be omnidirectional, it is preferred in the papillotome catheter that the field traverse a partial, yet fairly wide sector. Such a sectorial field may be achieved by longitudinally cutting outer conductive layer 52 at two spaced-apart locations corresponding to the desired sector after ultrasonic transducer has been mounted on member 40, and by electrically connecting center conductor 54 only to the portion of outer conductive layer 52 between these two cuts. Further, the cuts are made so that the desired sectorial field extends from the "inner" curve of the papillotome catheter, that is, the side of tube 10 along which wire 12 extends. The ultrasonic field may then be easily directed toward the retroduodenal artery by visualizing the position of wire 12.

The requirement of close proximity blood flow detection is addressed by the provision of groove 42 which provides an air backing for ultrasonic transducer 46. Since very little ultrasonic energy can be transmitted through air from the transducer because of the large difference in acoustic impedance between air and the piezoelectric material of the transducer, almost all of the ultrasonic energy produced by the transducer is radiated from the outer surface thereof covered with outer conductive layer 52. As a result, probe sensitivity is increased while avoiding entrapment of ultrasonic energy in member 40. If not compensated for, entrapment would produce multiple reverberations of transmitted ultrasonic energy in the probe which would take considerable time to damp, which damping time would block the Doppler circuit from analyzing received ultrasonic energy from blood flow in close proximity to the transducer. The use of air as a backing material is preferred because the small size of the probe makes it difficult to use another absorptive material as the backing material.

Close proximity detection is also enhanced by the annular, cylindrical form of ultrasonic transducer 46, which permits, in close proximity to the probe, angles of encounter other than 90° between the direction of blood flow and the direction of propagation of some of the transmitted ultrasonic energy. As is well known, no Doppler shift would be present if all angles of encounter between the blood flow and the transmitted ultrasonic field were 90°. The use of a highly directional transducer in the probe would make it difficult to detect blood flow if the probe were placed immediately adjacent a blood vessel. Taking the endoscopic papillotomy application as an example and referring back to FIG. 2, let it be assumed that retroduodenal artery 30 is within 1 mm of common bile duct 24. If probe 14 were to have a highly directional field, which can be visualized as a line in the plane of FIG. 2, it will be seen that blood flow in the retroduodenal artery in that field will always be perpendicular thereto. In contrast, the use of the unfocused radial field produced by transducer 46, which field can be visualized as a plane transverse to the plane of FIG. 2, will result in some of the blood in the retroduodenal artery encountering transmitted ultrasonic energy at angles other than 90°. Yet another advantage of a radial field is that such a field has fewer near-field maximum and minimum intensity points than a highly directional field, thereby further enhancing close proximity detection of blood flow.

Concerning safety, this requirement is addressed by the use of epoxy coating 62 that is preferably composed of a biocompatible, nontoxic and nonconductive epoxy resin. Because coating 62 covers the entirety of member 40, transducer 46, and inner conductor 54, it protects these elements from any fluids encountered within the body, maintains electrical isolation between the conductive elements of the probe and body tissue, and prevents the potentially toxic materials of the probe from coming into contact with body tissue. Since a portion of coating 62 extends over a portion of tube 10, coating 62 also assists in securing the probe to the tube.

The requirement of close proximity detection, as well as the requirements of range limiting, separation of venous and arterial flow and wall motion, and safety, are also addressed by the Doppler circuit of FIG. 16 as discussed hereinafter.

Figure 4:
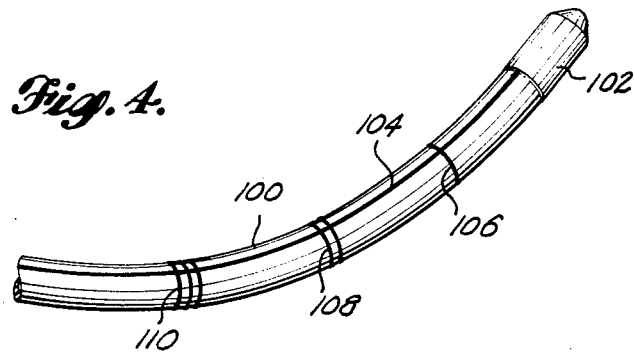
FIG. 4 is a pictorial view of another form of catheter including an ultrasonic probe that can be used in endoscopic papillotomy.

Referring now to FIG. 4, another form of a catheter usable in endoscopic papillotomy and other endoscopic and non-endoscopic applications includes an elongated, cylindrical tube 100 of flexible material having an ultrasonic probe 102 disposed at its tip. Along its exterior, tube 100 is provided with a longitudinally extending marking 104 that is preferably situated on an "inside" curve of the catheter formed by heat treating tube 100 to the curved configuration illustrated in FIG. 4. Preferably, probe 102 includes an annular, cylindrical transducer that has either an omnidirectional field transverse to the longitudinal axis of tube 100 or a transverse sectorial field aligned with marking 104 in a manner similar to the alignment of the sectorial field of transducer 46 with wire 12 in the papillotome catheter of FIG. 3. At regularly spaced intervals along its length, tube 100 is provided with transverse and circumferentially extending markings 106, 108 and 110, each of which indicates a predetermined incremental distance (such as 1 cm) from probe 102.

Figure 5:
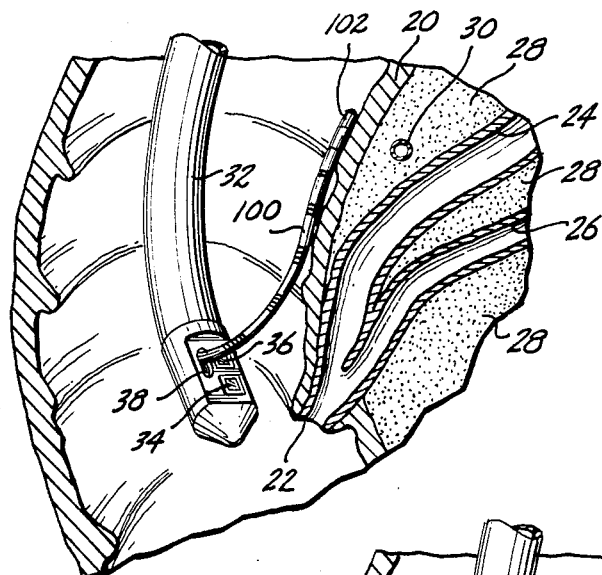
FIGS. 5 and 6 are schematic views illustrating the use of the catheter of FIG. 4 during endoscopic papillotomy.
Figure 6:
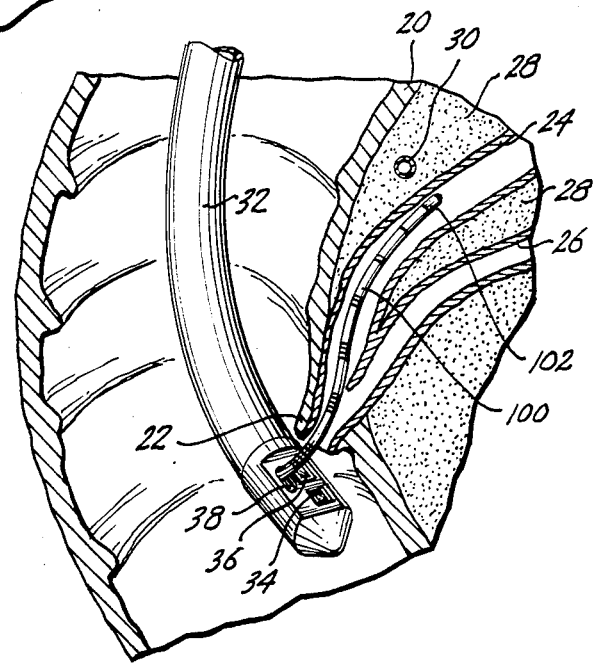

The catheter of FIG. 4 may be used in two different ways in endoscopic papillotomy, as illustrated in FIGS. 5 and 6.

In FIG. 5, the catheter of FIG. 4 preferably includes a probe 102 having a transverse omnidirectional field. The catheter is advanced through biopsy channel 38 of endoscope 32 until the catheter tip exits therefrom. The endoscope and catheter tips are then remotely manipulated, and the catheter concurrently advanced, so that the catheter slides along the side of duodenum 20 proximate retroduodenal artery 30. The process of catheter advancement continues until a Doppler signal characteristic of arterial blood flow is detected to indicate that probe 102 is proximate the retroduodenal artery. At this point, the transverse markings on tube 100 are visualized together with the papilla 22 in order to form an estimate of the location of the retroduodenal artery relative to the papilla.

In FIG. 6, the catheter preferably includes a probe 102 having a transverse sectorial field. The catheter tip is inserted into common bile duct 24, with the catheter being rotated so that the longitudinal marking on tube 100 faces the side of the common bile duct proximate retroduodenal artery 30, wherein the sectorial field is directed towards the retroduodenal artery. When a Doppler signal characteristic of arterial blood flow is detected, the location of the retroduodenal artery relative to the papilla may again be estimated by visualization of the transverse markings on tube 100 and of papilla 22.

In both procedures, the catheter of FIG. 4 is withdrawn from the endoscope after the relative location of retroduodenal artery 30 has been estimated. If the estimate indicates that there is no significant probability of cutting the retroduodenal artery during endoscopic papillotomy, a standard papillotome catheter is then advanced through the biopsy channel and used in a manner similar to that previously described for the papillotome catheter of FIG. 1.

FIGS. 7A, 7B and 7C illustrate one form of probe 102 that is substantially similar to the form of probe 14 illustrated in FIG. 3. As such, probe 102 includes a substantially cylindrical member 112 of a metallic material or of a plastic material covered with a conductive layer. An ultrasonic transducer 114 is disposed on member 112 and overlies a peripheral annular groove 116 therein.

The ultrasonic transducer has an inner conductive layer 118 electrically connected to member 112 and an outer conductive layer 120 to which is electrically connected a center conductor 122 of a microcoaxial cable 124 that passes through a central bore 126 of member 112 and whose outer conductive sheath 128 is electrically connected to member 112 within that bore. The outer diameter of member 112 is substantially equal to the inner diameter of tube 100, and member 112 is provided with spaced-apart, annular ridges 130 on its periphery which assist in securing probe 102 to tube 100 when member 112 is inserted into the end thereof. The catheter is completed by a coating 132 of a nonconductive epoxy resin that forms a thin layer over ultrasonic transducer 114 and the adjacent portion of tube 100 and that terminates in a smoothly rounded tip covering and insulating center conductor 122.

The ultrasonic field of the probe may be omnidirectional, as illustrated in FIG. 7A, or may be sectorial, as illustrated in FIG. 7B in which outer conductive layer 120 is provided with spaced-apart, longitudinal cuts 134, 136 that divide outer conductive layer into portions 120A, 120B and in which center conductor 112 is electrically connected only to portion 120A.

A catheter particularly adapted for non-endoscopic applications and for those endoscopic applications in which a directional ultrasonic field can be used is illustrated in FIGS. 8A and 8B. The catheter includes an elongated, cylindrical tube 140 of flexible material and an ultrasonic probe 142 disposed at the tip of tube 140. Probe 142 includes a substantially cylindrical member 144 of a metallic material or of a plastic material covered with a conductive layer that has a smoothly rounded tip. On one side, member 144 has a flat surface 146. A rectangular recess containing a flat, ultrasonic transducer 148 extends into member 144 from surface 146, and a further recess 150 underlies ultrasonic transducer 148. An inner conductive layer 152 of transducer 148 is electrically connected to member 144, and an outer conductive layer 154 of transducer 148 is electrically connected to a center conductor 156 of a microcoaxial cable 158 disposed within an off-axis bore 160 in member 144 that terminates adjacent surface 146. Outer conductive sheath 162 of cable 158 is electrically connected to member 144. At its end away from its smoothly rounded tip, member 144 has an outer diameter that is substantially equal to the inner diameter of tube 140. Spaced-apart, annular ridges 164 on the periphery of member 144 assist in retaining probe 142 on the tip of tube 140 when member 144 is inserted therein. The catheter is completed by a coating 166 of a nonconductive epoxy resin that forms a thin layer over all exterior surfaces of member 144, transducer 148, center conductor 156, and the adjacent portion of tube 140.

As previously discussed, another situation in which it is desirable to detect blood flow is in the evaluation and treatment of esophageal varices. Referring now to FIG. 9, a flexible, end-viewing endoscope 170 has been inserted into esophagus 172. Endoscope 170 has optical fibers 174 and 176 terminating in an end face thereof that permit the interior of esophagus 172 to be visualized, and a biopsy channel 178 also terminating in the end face through which a catheter or other device may be passed. On the inner surface of esophagus 172, a number of protrusions 180, 182 and 184 are present. In order to determine whether any of the protrusions is a varix, the protrusion is first visualized by remote manipulation of the endoscope tip. Then, a catheter including an elongated tube 186 of flexible material and an ultrasonic probe 188 disposed at the tip thereof is advanced through biopsy channel 178 until the catheter tip exits therefrom, and the endoscope tip is further manipulated and the catheter is further advanced until ultrasonic probe 188 comes to rest on the visualized protrusion, such as protrusion 184. The ultrasonic field provided by ultrasonic probe 188 may be either transverse to or parallel to the longitudinal axis of tube 186. The probe may be constructed in a manner similar to that illustrated in FIGS. 7A-7C or in the manner discussed hereinafter in conjunction with FIGS. 10A, 10B and 11.

When the catheter is in place, the Doppler signal obtained therefrom is monitored for that characteristic of venous flow. If such a Doppler signal is obtained, the protrusion, such as protrusion 184, has been positively identified as a varix. The catheter is then withdrawn from biopsy channel 178 and another catheter having a hollow needle disposed at its tip is advanced along the biopsy channel until the needle enters the varix. A sclerosing agent is then injected into the varix through the catheter and needle in order to thrombose or clot the varix. Thereafter, the catheter and needle are withdrawn and the catheter including tube 186 and ultrasonic probe 188 is reinserted into biopsy channel 178 and advanced therethrough into contact with the varix. By monitoring the Doppler signal obtained from probe 188, an indication may be obtained as to whether the varix has been completely or partially thrombosed. If the varix has been completely thrombosed, no Doppler signal characteristic of venous flow will be present.

Referring now to FIGS. 10A and 10B, one form of ultrasonic probe 188 that provides a radial field extending over a sector of greater than 180° relative to the catheter longitudinal axis is illustrated. A substantially cylindrical member 190 of a metallic material or of a plastic material covered with a conductive layer has a central, substantially rectangular projection 192 extending from one end thereof and coaxial therewith. A second substantially cylindrical member 194 of a metallic material or of a plastic material covered with a conductive layer has a central bore 196 and a transverse, substantially rectangular bore 198 extending from its periphery to central bore 194. Members 190 and 194 are assembled so that projection 192 is received within transverse bore 198, whereby the longitudinal axis of member 194 is transverse to that of member 190. Around its periphery, member 194 has formed therein an annular groove 200. An ultrasonic transducer 202 consisting of an annular, semicylindrical ring is fitted over member 194 and overlies groove 200. An inner conductive layer 204 of ultrasonic transducer 202 is electrically connected to member 194, and an outer conductive layer 206 of ultrasonic transducer 202 is electrically connected to the center conductor 208 of a microcoaxial cable 210 that passes through an off-axis bore 212 within member 190. An outer conductive sheath 214 of cable 210 is electrically connected to member 190 within bore 212. The outer diameter of member 190 is substantially equal to the inner diameter of tube 186, and member 190 is provided with spaced-apart, annular ridges 216 about its periphery which assist in retaining ultrasonic probe 188 on the tip of tube 186 when member 190 is inserted therein. The catheter is completed by a coating 218 of a nonconductive epoxy resin covering transducer 202, member 194, member 190, and center conductor 208, and extending over the adjacent portion of tube 186.

Another form of ultrasonic probe 188 providing a highly directional field parallel to the catheter longitudinal axis is illustrated in FIG. 11. A substantially cylindrical member 220 of a metallic material or of a plastic material covered with a conductive layer has a cylindrical recess 222 in one end and coaxial with its longitudinal axis. A flat, circular ultrasonic transducer 224 is disposed on that end of member 220 and overlies recess 224. An inner conductive layer 226 of the ultrasonic transducer 224 is electrically connected to member 220, and an outer conductive layer 228 of ultrasonic transducer 224 is electrically connected to the center conductor 230 of a microcoaxial cable 232 passing through a central bore 234 of member 220. An outer conductive sheath 236 of cable 232 is electrically connected to member 220 within bore 234. The catheter is completed by a coating 238 of a nonconductive epoxy resin that forms a thin layer over transducer 224 and member 220 and that extends over the adjacent portion of tube 186.

To this point, the evaluation and treatment of esophageal varices has been discussed with respect to the use of two separate catheters. If desired, these catheters may be combined into a single sclerosing catheter, as illustrated in FIG. 12. The sclerosing catheter includes an elongated tube 240 of flexible material having an ultrasonic probe 242 disposed at its tip, and a needle 244 that can be remotely projected from or withdrawn within the tip of probe 242. In the evaluation of esophageal varices, the needle is preferably withdrawn. The sclerosing catheter is advanced and positioned, and the Doppler signal obtained therefrom is monitored for that characteristic of venous flow, in a manner similar to that previously described in conjunction with FIG. 9. When a varix has been positively identified, needle 244 is remotely projected from probe 242 into the varix. A sclerosing agent is then injected into the varix through needle 244 and the Doppler signal obtained from probe 242 is monitored to determine whether complete or partial thrombosis has been obtained.

Three exemplary forms of the sclerosing catheter in FIG. 12 are illustrated in FIGS. 13, 14 and 15.

In FIGS. 13, probe 242 includes a substantially cylindrical member 246, of a metallic material or of a plastic material having a conductive layer thereon, that has a frustoconical tip. Around its periphery, member 246 is provided with an annular groove 248. An annular, cylindrical ultrasonic transducer 250 is fitted over member 246 and overlies groove 248. An inner conductive layer 252 of ultrasonic transducer 250 is electrically connected to member 246, and an outer conductive layer 254 of ultrasonic transducer 248 is electrically connected to a lead 256 which is passed through a notch in the periphery of member 246 away from its frustoconical tip. A second lead 258 is electrically connected to member 246. Leads 256 and 258 are twisted along their length from probe 242 to the distal end of tube 240 (not illustrated) and exit therefrom. The outer diameter of member 246 away from its tip is substantially equal to the inner diameter of tube 240, and member 246 is provided with spaced-apart, annular ridges 259 about its periphery which assist in retaining ultrasonic probe 242 on the tip of tube 240 when member 246 is inserted therein. A coating 260 of a nonconductive epoxy resin forms a thin layer over the frustoconical tip of member 246, ultrasonic transducer 250 and lead 256, and the adjacent portion of tube 240.

Member 246 is provided with a central bore 262 whose diameter is slightly greater than that of needle 244. Needle 244 is dispose for translative motion within bore 262 and its distal end is received within the end of an elongated tube 264 extending within and along the length of tube 240 and exiting from the distal end thereof. Preferably, tube 264 is of a flexible material that is yet rigid enough to permit needle 244 to be projected from and withdrawn into probe 242 by the remote application of force.

The ultrasonic field provided by the form of ultrasonic probe 242 in FIG. 13 is transverse and substantially normal to the longitudinal axis of tube 240 and preferably is omnidirectional. When a protrusion has been positively identified as a varix, the sclerosing agent is injected in the varix via tube 264 and needle 244.

The form of ultrasonic probe 242 in FIG. 14 is similar to that of FIG. 13, with the following exceptions. First, the member thereof is provided with an annular groove 270 on its frustoconical tip. Secondly, an annular, frustoconical ultrasonic transducer 272 is fitted on the tip so as to overlie groove 270. Third, a longitudinal notch 274 is cut along the periphery of the member so as to provide a passageway for the lead connected to the outer conductive layer of the ultrasonic transducer. The ultrasonic field provided by the form of ultrasonic probe 242 in FIG. 14 is transverse and oblique to the longitudinal axis of tube 240 and preferably is omnidirectional.

The form of ultrasonic probe 242 in FIG. 15 includes a substantially cylindrical member 275 of a metallic material or of a plastic material covered with a conductive layer that has a cylindrical recess 276 formed in one end and coaxial with the longitudinal axis of member 275. A flat, circular ultrasonic transducer 278 is disposed on that end of member 275 and overlies recess 276. An inner conductive layer 282 of ultrasonic transducer 278 is electrically connected to member 275, and an outer conductive layer 282 of ultrasonic transducer 278 is electrically connected to the center conductor 284 of a microcoaxial cable 286 that passes through an off-axis bore 288 in member 275. An outer conductive sheath 290 of cable 286 is electrically connected to member 275 within bore 288. The outer diameter of member 275 is substantially equal to the inner diameter of tube 240, and member 275 is provided with spaced-apart, annular ridges 291 about its periphery that assist in retaining ultrasonic probe 242 on the tip of tube 240 when member 275 is inserted therein. A coating 292 of epoxy resin covers ultrasonic transducer 278, member 275, center conductor 284, and the adjacent portion of tube 240.

Member 275 is provided with a central bore 294 extending to recess 276. Likewise, ultrasonic transducer 278 and coating 292 are also provided with a central bore 296 that is coaxial with bore 294. Needle 244 is disposed for translative movement within bores 294 and 296, and the distal end thereof is inserted within the end of tube 264 as previously described. The ultrasonic field provided by the form of ultrasonic probe 242 in FIG. 15 is substantially parallel to the longitudinal axis of tube 240 and is highly directional along that axis.

Figure 16:
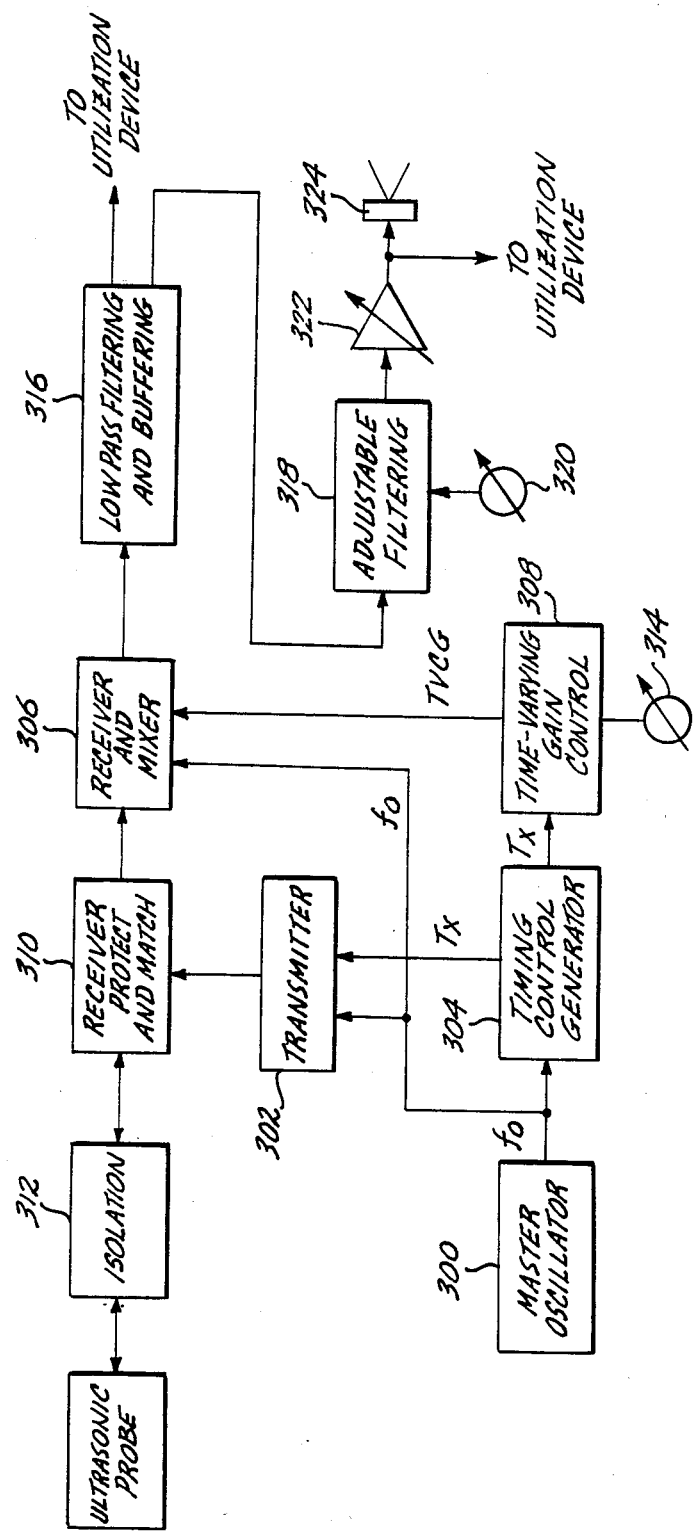
FIG. 16 is a block diagram of a Doppler circuit to be used with the catheters previously discussed.

With reference now to the Doppler circuit in FIG. 16, a master oscillator 300 provides an output signal consisting of a sine wave or a square wave having a fundamental frequency $f_0$. The output signal for master oscillator 300 is applied to a transmitter 302, a timing control generator 304, and a first input of a receiver and mixer 306. Timing control generator 304 functions to divide the pulses in the output signal from master oscillator 300 so as to provide an output signal Tx that has a duration equal to the desired duration of a burst of ultrasonic energy from the ultrasonic transducer and that occurs at a predetermined repetition rate. Signal Tx is applied to transmitter 302 and to a time-varying gain control circuit 308. In response to and for the duration of each signal Tx, transmitter 302 provides a transmitted signal comprising a relatively high amplitude, alternating current, electrical signal at frequency $f_0$, which is applied to a receiver protect and match circuit 310 that is coupled to a second input of receiver and mixer 306 and to an isolation circuit 312. Receiver protect and match circuit 306 functions to minimize the amplitude of the transmitted signal that is applied to the second input of receiver and mixer 306 and to match the impedance of that input to the impedance of isolation circuit 312. The transmitted signal passes through receiver protect and match circuit 310 and from there is coupled through isolation circuit 312 and the catheter cable or leads to the ultrasonic probe. In response to the transmitted signal, the ultrasonic transducer within the ultrasonic probe emits a short burst of ultrasonic energy equal in duration to that of signal Tx. Any returns of ultrasonic energy from objects within the ultrasonic field that occur upon termination of the transmitted burst are converted by the ultrasonic transducer into a relatively low amplitude, received electrical signal that is coupled through isolation circuit 312 and receiver protect and match circuit 310 to the second input of receiver and mixer 306.

Within receiver and mixer 306, the received signal is amplified by a gain controlled by an output signal TVCG from time-varying gain control circuit 308. This gain varies with time in a manner hereinafter described, and the variation may be adjusted by a manual control 314 of circuit 308. After amplification, the received signal is mixed in receiver and mixer 306 with the output signal from master oscillator 300 at frequency $f_0$, whereby an output signal from receiver and mixer 306 contains both sum and difference frequencies of the received signal and of the output signal from master oscillator 300. The sum frequencies, being of no interest, are eliminated in a low-pass filtering and buffering circuit 316. The difference frequencies, or, the Doppler frequencies resulting from relative motion between objects within the ultrasonic field and the ultrasonic transducer, are further filtered within circuit 316 to remove the repetition rate of signal Tx and other undesired signals, and then buffered. The output signal from low-pass filtering and buffering circuit 316 is therefore the Doppler signal which may be applied to a desired utilization device or may be applied to an adjustable filtering circuit 318 for bandpass filtering selected by a control 320. The filtered Doppler signal available at the output of adjustable filtering circuit 318 is further amplified by an adjustable-gain amplifier 322 and then audibly reproduced by a loudspeaker 324 or applied to an appropriate utilization device.

As previously discussed, the requirements of close proximity detection, range limiting, separation of venous flow from arterial flow and wall motion, and safety must be addressed in the successful detection of blood flow within the body. The Doppler circuit in FIG. 16 treats these requirements in the following manner.

In order to enhance close proximity detection, the receiver and mixer 306 must be prevented from becoming saturated during transmission and must be capable of rapid recovery following transmission. First, the fractional bandwidth of the apparatus, that is, the apparatus bandwidth divided by frequency $f_0$, must be chosen to provide for rapid recovery of receiver and mixer 306. A preferred fractional bandwidth is $\frac{1}{8}$. Second, the power level of the transmitted signal must be kept as low as possible to limit the power level that has to be recovered therefrom. By choosing a frequency $f_0$ that is as high as possible, the amount of reflected ultrasonic energy from objects such as blood cells per unit of transmitted signal power may be increased, since the amount of reflected energy is related to the fourth power of the transmitted signal frequency. A preferred frequency $f_0$ is 8 MHz. Third, time-varying gain control circuit 308 is constructed so as to substantially attenuate the gain of receiver and mixer 306 during signal Tx and to thereafter increase the gain at a rate chosen to compensate for ultrasonic energy loss due to cylindrical dispersion as the transmitted ultrasonic energy propagates away from the ultrasonic transducer, due to spherical dispersion of the ultrasonic energy that returns to the ultrasonic transducer, and due to tissue attenuation of the ultrasonic energy that occurs between the transducer and the objects of interest. Preferably, the time variation in gain that is controlled by signal TVCG from circuit 308 following termination of signal Tx adheres to the following relationship:

$$\text{gain} = K \left( \frac{.075 T^{1.5}}{e^{-.21 T}} \right)$$

where K is an arbitrary constant and T is the time after termination of signal Tx, in microseconds.

Turning now to the requirement of range limiting, it has been found to be necessary in the endoscopic applications previously discussed to limit the maximum range or distance from the probe over which blood flow is detected in order to insure that the detected blood flow is from the biological structure of interest. In endoscopic papillotomy, the maximum range is preferably limited to 5 mm from the ultrasonic probe. In the evaluation of esophageal varices, the maximum range is preferably limited to 4 mm or less in order to avoid venous flow through any varix being masked by arterial flow through arteries or other blood vessels outside the esophagus. Typically, most varices occur in the region of the esophagus adjacent the heart where large arterial flow is present.

Range limiting is accomplished in the Dopper circuit of FIG. 16 by time-varying gain control circuit 308 which substantially attenuates the gain of receiver and mixer 306 by signal TVCG at a time following termination of signal Tx that corresponds to the desired maximum range, which attenuation time can be selected by control 314.

The next requirement to be addressed is the separation of venous flow, arterial flow and wall motion. In the Doppler circuit of FIG. 16, this requirement is met by adjustable filtering circuit 318. In an apparatus operating at a frequency $f_0$ of 8 MHz and using the ultrasonic probes previously described, it has been determined that the Doppler frequencies resulting from wall motion due to cardiac blood pulsation are typically below 200 Hz, that the Doppler frequencies resulting from venous flow are primarily in the range of 200 Hz to 1,500 Hz and occasionally as high as 2,000 Hz, and that the Doppler frequencies resulting from arterial flow are primarily in the range of 500 Hz to 5,000 Hz and occasionally as high as 8,000 Hz. Although the Doppler frequencies resulting from venous flow and arterial flow do overlap, the time variations of the corresponding Doppler signals permit arterial flow to be distinguished from venous flow, with arterial flow being pulsatile at the heart rate of the patient and venous flow being continuous in some cases and modulated by respiratory action in other cases. Adjustable filtering circuit 318 includes a plurality of bandpass filters which allow the user to select, through control 320, either primarily venous flow (200 Hz–1,500 Hz), arterial and venous flow (500 Hz–5,000 Hz), or primarily arterial flow (2,000 Hz–5,000 Hz). Preferably, these bandpass filters have a roll-off of at least 40 dB/decade and are embodied in a sampled type of switching filter that is synchronized to master oscillator 300.

Providing electrical isolation is mandatory in endoscopic and other intracorporeal applications in order to provide safety to the patient. This isolation is provided by isolation circuit 312, embodiments of which are seen in FIGS. 17–20.

Referring to FIG. 17, the center conductor 330 of a microcoaxial cable 332 passing through the tube 333 of the catheter and going to the ultrasonic probe is connected at its end away from the probe to one side of the primary winding 334 of a transformer 336, and the outer conductive sheath 338 of cable 332 is connected to the other side of primary winding 334. One side of a secondary winding 338 of transformer 336 is connected to the center conductor 340 of a microcoaxial cable 342, and the other side of secondary winding 338 is connected to the outer conductive sheath 344 of cable 342. Cable 342 terminates in a connector 346 that is adapted to mate with a corresponding connector going to receiver protect and match circuit 310.

Primary winding 334 and secondary winding 338 are wound on a core 348 of transformer 336, as illustrated in FIG. 18. Core 348 consists of an elongated block of ferromagnetic material having spaced-apart, longitudinal bores 350 and 352 extending therethrough. Both primary winding 334 and secondary winding 338 are wound around the intermediate portion of core 348 between bores 350 and 352. The material of core 348 and its configuration provide very high primary to secondary magnetic coupling and therfore high efficiency transformation. A preferred example of such a core is that available from Fair-Rite Products as Model #2861006802. At the apparatus frequency $f_0$ that is preferred (e.g., 8 MHz), the primary inductance of the ultrasonic transducer under an open circuit load is high enough to require only two loops in the primary winding and only two loops in the secondary winding. By the use of this minimum number of loops, primary to secondary capacitive coupling is minimized. Minimization of capacitive coupling is further minimized by choosing a very small diameter wire for both windings (e.g., 32 gauge) which is surrounded by insulation that is as thick as 2 mm.

The introduction of an isolation circuit such as that illustrated in FIG. 17 between the ultrasonic probe and the Doppler circuit might result in the introduction of radio frequency interference (RFI) into the Doppler circuit, inasmuch as microcoaxial cable 332 then functions as an antenna for radio frequency energy. The minimization of primary to secondary capacitive coupling, in addition to providing electrical isolation, also minimizes any transfer of such RFI to the Doppler circuit.

The isolation circuits in FIGS. 19 and 20 provide additional suppression of RFI over that circuit in FIG. 17.

Referring to FIG. 19, a pair of microcoaxial cables 360 and 362 extend through tube 363 of the catheter to the ultrasonic probe, with the center conductors 364 and 366 thereof being electrically connected to the ultrasonic transducer therein and with the outer conductive sheaths 368 and 370 being connected to each other. At their ends away from the ultrasonic probe, cables 360 and 362 are passed into a conductive housing 372 in which is disposed a transformer having a core 376, a center-tapped primary winding 378, and a secondary winding 380. Center conductors 364 and 366 of cables 360 and 362 are connected to respective ends of primary winding 378, and outer conductive sheaths 368 and 370 are connected to the center tap thereof.

One side of the secondary winding 380 is connected to housing 372 and to a source of ground potential, and the other side of secondary winding 380 is connected to a connector 382 which may be used to connect to the receiver protect and match circuit 310. Preferably, transformer 374 is constructed in a manner substantially identical to that of transformer 336 in FIG. 18, with the exception that the center tap of the primary winding is provided by removing a portion of the insulation from the primary winding adjacent one side of the transformer core (e.g., to the left in FIG. 18) and by soldering the outer conductive sheaths of the microcoaxial cables thereto.

The principal advantage of the isolation circuit in FIG. 19 over that in FIG. 17 is that any RFI is induced in both center conductors 364 and 366 and is applied to opposing sides of primary windings 378, thereby leading to substantial RFI cancellation and minimization of the development of differential RFI on secondary winding 380.

The isolation circuit in FIG. 19 is disadvantageous in that it requires two microcoaxial cables to be passed through the tube of the catheter. The isolation circuit in FIG. 20 avoids this disadvantage, as follows. A twisted pair of conductors 390 and 392 extend through tube 393 of the catheter to the ultrasonic probe. Conductors 390 and 392 are connected at their ends away from the probe to respective ends of the primary winding 394 of a transformer 396 located within a conductive housing 398. Transformer 396 is provided with a core 400 and with a secondary winding 402. Preferably, transformer 396 is substantially identical to transformer 336 illustrated in FIG. 18. One side of secondary winding 402 is connected to the center conductor 404 of a microcoaxial cable 406 and the other side of secondary winding 402 is connected to the center conductor 408 of a microcoaxial cable 410. Outer conductor sheaths 412 and 414 of cables 406 and 410 are connected to each other and to housing 398. At their ends away from housing 398, cables 406 and 410 are passed into a conductive housing 416 in which is disposed a transformer 418 having a core 420, a center-tapped primary winding 422 and a secondary winding 424. Center conductors 404 and 408 are connected to respective sides of primary winding 422, and outer conductive sheaths 412 and 414 are connected to the center tap of primary winding 422 and to housing 416. One side of secondary winding 424 is connected to ground and to housing 416, and the other side of secondary winding 424 is connected to a connector 426 that may be connected to receiver protect and match circuit 310. Transformer 418 is constructed in a manner similar to transformer 374 in FIG. 19.

Transformer 396 functions in a manner identical to transformer 336 in FIG. 17, in minimizing primary to secondary capacitive coupling thereacross. Any RFI that is yet coupled across transformer 396 is applied equally to center conductors 404 and 408, and any additional RFI present in the region of cables 406 and 410 is likewise equally induced in those conductors. As with the isolation circuit of FIG. 19, this RFI is supplied to opposite sides of primary winding 422, thereby leading to RFI cancellation and minimization of differential RFI on secondary winding 424.

While the invention has been described with reference to a preferred embodiment and alternative forms thereof, it is to be clearly understood by those skilled in the art that the invention is not limited thereto and that the scope of the invention is to be interpreted only in conjunction with the appended claims.

The embodiments of the invention in which an exclusive property or privilege are claimed is as follows:

1. A method for determining the location of the retroduodenal artery relative to the papilla of Vater during endoscopic papillotomy, said method comprising the steps of:
   inserting a flexible, side-viewing endoscope into the duodenum;
   visualizing the papilla through the endoscope;
   passing a catheter including an ultrasonic probe having a transverse, sectorial, range-limited field through a biopsy channel of the endoscope, through the papilla, and into the common bile duct so that said ultrasonic field is directed towards the retroduodenal artery;
   advancing the catheter and monitoring a Doppler signal obtained from the probe until the Doppler signal is characteristic of arterial blood flow; and,
   visualizing, through the endoscope, the amount by which the catheter has been advanced past the papilla.

2. A method for determining the location of the retroduodenal artery relative to the papilla of Vater during endoscopic paillotomy, said method comprising the steps of:
   inserting a flexible, side-viewing endoscope into the duodenum;
   visualizing the papilla through the endoscope;
   passing a catheter including an ultrasonic probe having a transverse, range-limited ultrasonic field through a biopsy channel of the endoscope and into contact with the duodenum;
   advancing the catheter along the duodenum and monitoring a Doppler signal obtained from the probe until the Doppler signal is characteristic of arterial blood flow; and,
   visualizing, through the endoscope, the location of the probe relative to the papilla.

3. A method for evaluating esophageal varices, said method comprising the steps of:
   inserting a flexible, end-viewing endoscope into the esophagus;
   visualizing a protrusion in the esophagus through the endoscope;
   passing a catheter including an ultrasonic probe having a range-limited ultrasonic field through a biopsy channel of the endoscope and into the esophagus until the probe contacts the protrusion; and
   monitoring a Doppler signal obtained from the ultrasonic probe for that Doppler signal characteristic of venous blood flow.

4. A method for identifying and monitoring an intracorporeal biological structure, said method comprising the steps of:
   inserting an endoscope into the body;
   visualizing, through the endoscope, the location of the biological structure;
   passing a catheter including an ultrasonic probe through a biopsy channel of the endoscope and into proximity to the biological structure; and,
   monitoring a Doppler signal obtained from the ultrasonic probe for that Doppler signal characteristic of blood flow in the biological structure.

* * * * *

UNITED STATES PATENT AND TRADEMARK OFFICE
CERTIFICATE OF CORRECTION

PATENT NO. : 4,582,067

DATED : April 15, 1986

INVENTOR(S) : Fred E. Silverstein et al.

It is certified that error appears in the above-identified patent and that said Letters Patent is hereby corrected as shown below:

Column 3, line 42, "Dopper" should be --Doppler--.

Column 6, line 63, "valuation" should be --evaluation--.

Column 13, line 42, "FIGS." should be --FIG.--.

Column 15, line 56, "applied" should be --supplied--.

Column 16, line 50, "Dopper" should be --Doppler--.

Column 17, line 46, "therfore" should be --therefore--.

Column 18, line 36, "windings" should be --winding--.

Column 20, line 3, "paillotomy" should be --papillotomy--.

Signed and Sealed this

Fifteenth Day of July 1986

[SEAL]

Attest:

DONALD J. QUIGG

Attesting Officer

Commissioner of Patents and Trademarks